United States Patent
Sakamoto

(10) Patent No.: US 9,072,869 B2
(45) Date of Patent: Jul. 7, 2015

(54) VIBRATION IMPARTING DEVICE

(71) Applicant: Satoru Sakamoto, Hyogo (JP)

(72) Inventor: Satoru Sakamoto, Hyogo (JP)

(*) Notice: Subject to any disclaimer, the term of this patent is extended or adjusted under 35 U.S.C. 154(b) by 0 days.

(21) Appl. No.: 14/037,789

(22) Filed: Sep. 26, 2013

(65) Prior Publication Data

US 2014/0094779 A1    Apr. 3, 2014

(30) Foreign Application Priority Data

Sep. 28, 2012  (JP) ................. 2012-216464

(51) Int. Cl.
*A61B 17/20* (2006.01)
*A61M 25/01* (2006.01)
*A61B 17/3207* (2006.01)
*A61B 17/22* (2006.01)

(52) U.S. Cl.
CPC ........... *A61M 25/01* (2013.01); *A61M 25/0116* (2013.01); *A61B 17/3207* (2013.01); *A61B 2017/22042* (2013.01); *A61B 2017/22075* (2013.01); *A61B 2017/22094* (2013.01)

(58) Field of Classification Search
CPC ................ A61B 17/3207; A61B 2017/22075; A61B 2017/22094; A61B 2017/22038; A61B 2017/22004
USPC ...................................... 604/22, 510
See application file for complete search history.

(56) References Cited

U.S. PATENT DOCUMENTS 5,647,851 A * 7/1997 Pokras ............. 604/131

FOREIGN PATENT DOCUMENTS

| JP | 2009-000586 A | 1/2009 |
| JP | 2009-233019 A | 10/2009 |

* cited by examiner

*Primary Examiner* — Kevin C Sirmons
*Assistant Examiner* — Deanna K Hall
(74) *Attorney, Agent, or Firm* — Kubotera & Associates, LLC

(57) ABSTRACT

The present invention discloses a vibration imparting device having an attachment mechanism 5 that supports a guiding catheter 10*a* to be inserted into a body, and a vibrating portion 4 that is located outside the body and imparts vibration of non-ultrasonic frequency to the guiding catheter 10*a* via the attachment mechanism 5. That enables a catheter to be easily inserted into a lesion area of the body.

10 Claims, 4 Drawing Sheets

VIBRATION IMPARTING DEVICE

CROSS-REFERENCES TO RELATED APPLICATIONS

The present application is related to the Japanese Patent Application No. 2012-216464, Sep. 28, 2012, the entire disclosure of which is expressly incorporated by reference herein.

BACKGROUND OF THE INVENTION

1. Field of the Invention

The present invention relates to a vibration imparting device.

2. Description of the Related Art

In clinical practice throughout the world, percutaneous surgery is widely performed on a hollow organ in a living body, such as a coronary artery or a peripheral artery or vein.

For example, in the percutaneous surgery, a method to form a hollow structure, including an artery, a vein or a coronary artery, is known. The hollow structure is formed by inserting a catheter through a lesion area where a blood vessel wall becomes calcified or narrows, together with a wire or the like (mainly a guide wire) which is inserted ahead of the catheter.

Patent document 1: Japanese Patent Application Publication No. 2009-233019

Patent document 2: Japanese Patent Application Publication No. 2009-000586

BRIEF SUMMARY OF THE INVENTION

For example, when an operator tries to insert the catheter through the lesion area, if the catheter is caught in the lesion area or if the catheter to support an insert is deformed, it may be difficult to insert the catheter, the guide wire, or other similar medical appliances through the lesion area. In such a case, the operator may try to insert the catheter by manually vibrating the catheter using surgical techniques. However, because of reasons such as instability or lack of pliability of a backup catheter (guide catheter), the catheter or the wire to be inserted may be damaged or may not reach the lesion area to be treated. If that happens, the catheter is replaced to another one in order to retry to insert the catheter through the lesion area. However, cost of medical supplies often increases if the catheter is replaced several times, because the catheter is relatively expensive. In addition, treatment often ends in failure. One aspect of the present invention aims to enable to safely and easily insert the catheter thorough hollow organs in a living body, including the above mentioned blood vessels. Also, the present invention aims to improve a success rate of treatment by increasing the success rate even in difficult cases, which conventionally ended in failure.

In order to achieve the aims above, the present disclosure provides a vibration imparting device. The vibration imparting device has a supporting portion that supports an insertion device to be inserted into a body and a vibrating portion that is located outside the body to impart vibration of non-ultrasonic frequency to the insertion device via the supporting portion.

One aspect of the present invention enables the catheter to be easily inserted.

DETAILED DESCRIPTION OF THE INVENTION

Figure 1:
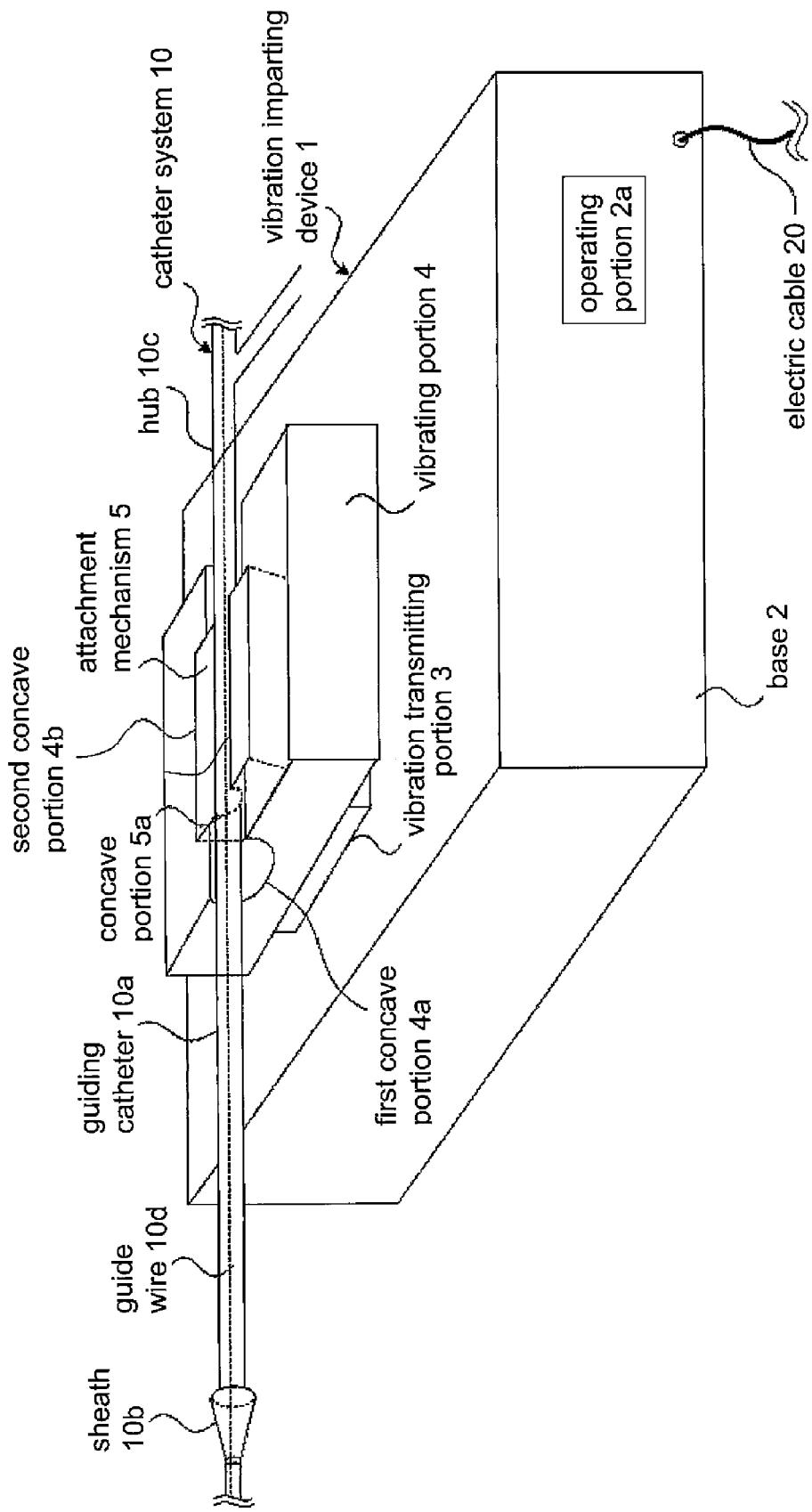
FIG. 1 shows a vibration imparting device of the present embodiment.

Hereafter, a vibration imparting device of the present embodiment will be explained in detail with reference to drawings. In the present embodiment, an example of using the vibration imparting device on a guiding catheter for coronary artery vessel and a catheter for insertion treatment is explained. The catheter for insertion treatment includes a catheter with a balloon for expanding function, a catheter for placing a stent at a treatment site, a catheter for observing blood vessels, a catheter for aspirating a thrombus in blood vessels, and other types of catheters. In addition, the type of the catheter available for the vibration imparting device is not limited to the above catheters. The vibration imparting device is also available for catheters used for other blood vessels, catheters used for other hollow organs than the blood vessels. Hereafter, embodiments of the present invention will be explained. FIG. 1 shows a vibration imparting device of the present embodiment.

A catheter system 10 shown in FIG. 1 has a guiding system (hereafter referred to as a guiding catheter) 10a, which is composed of a body of the guiding catheter and a branch connector, a sheath 10b, and a hub 10c. The guiding catheter 10a is an example of the insertion device. The guiding catheter 10a is a catheter placed extending from a puncture site to an entrance of the coronary artery.

The sheath 10b is inserted into body cavities of a patient, such as arteries, veins, and other lumens. The sheath 10b has a shape of long length and small diameter so as to be easily inserted into the body cavities such as blood vessels. Inside the sheath 10b, a path for a guide wire 10d is formed so as to insert the guide wire 10d. The sheath 10b has a rubber valve to prevent blood from flowing backwards.

Figure 2:
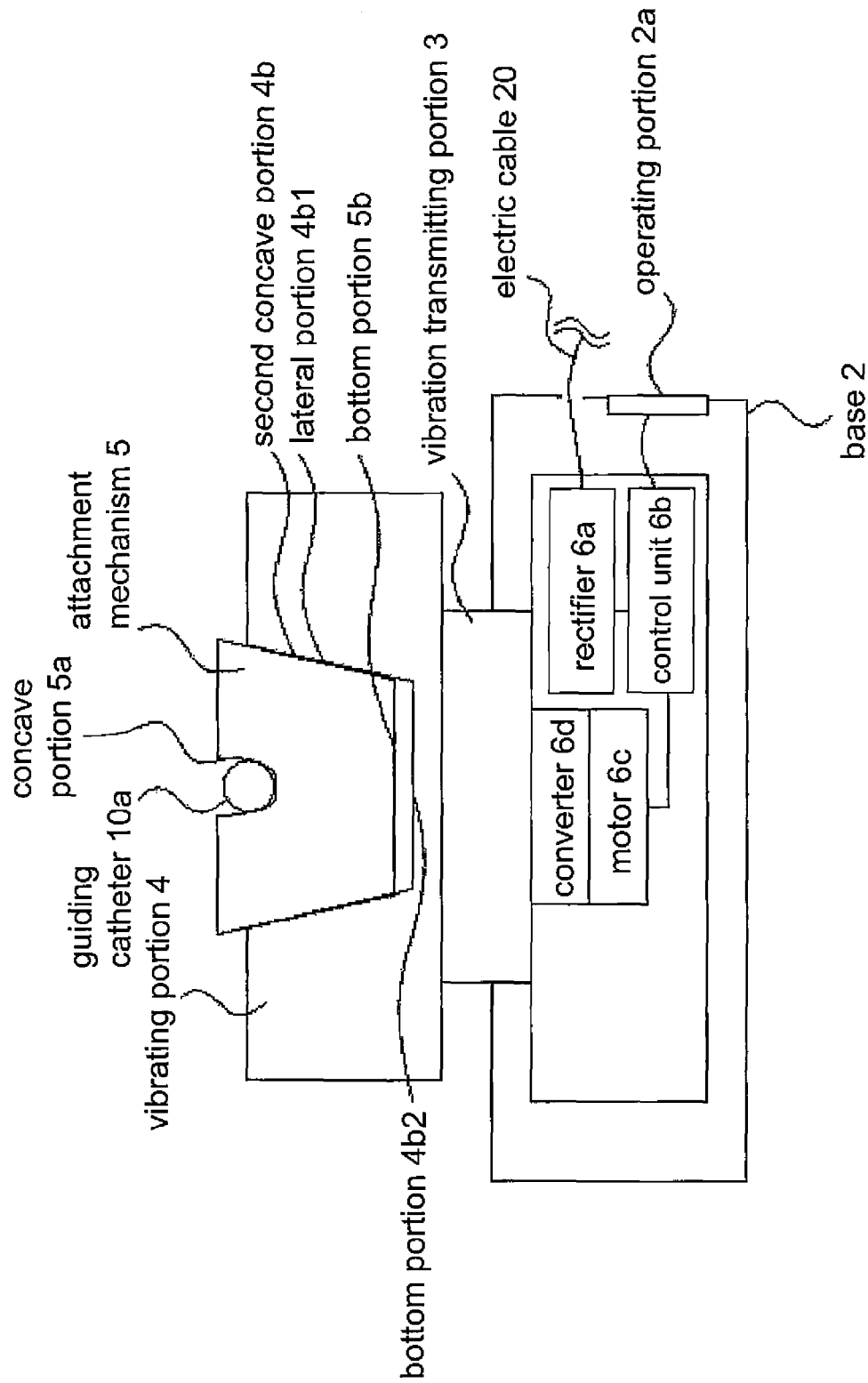
FIG. 2 shows a cross-sectional view of the vibration imparting device.

The hub 10c is not inserted into the body cavities and placed nearer the operator because the operator operates the hub 10c. The operator uses the hub 10c to adjust an amount of insertion of the sheath 10b, or to inject normal saline or the like. The injected normal saline or the like is supplied to the body cavities via the sheath 10b. Hereafter, a structure of the vibration imparting device will be explained with reference to FIGS. 1 and 2. FIG. 2 shows a cross-sectional view of the vibration imparting device. A vibration imparting device 1 has a base 2, a vibration transmitting portion 3, a vibrating portion 4, an attachment mechanism 5, and an actuator 6.

The base 2 is made of, for example, acrylonitrile-butadiene-styrene (ABS) resins, high molecular compounds such as a plastic resin, or metals such as an aluminum. An operating portion 2a is provided on a part of the base 2 so as to adjust parameters such as a vibration frequency or a vibration wavelength. The operator can specify the desired vibration frequency and the vibration wavelength by operating the operating portion 2a.

The operating portion 2a has a switch (not illustrated) to turn on/off the vibration imparting device 1, a monitor to display a screen enabling the operator to select a preliminarily specified operation mode of the vibration imparting device 1, and buttons to specify the parameters of actual vibration such as the vibration frequency or the vibration wavelength. In addition, the operating portion 2a also has switches to start or stop vibrating. Inside the base 2, the actuator 6 is provided to generate a vibration of a certain frequency.

The actuator 6 has a rectifier 6a, a control unit 6b, a motor 6c, and a converter 6d.

The rectifier 6a rectifies an AC voltage, which is supplied from an AC power source via an electric cable 20, into a DC voltage. The control unit 6b is connected to the operating portion 2a.

Based on control signals supplied from the operating portion 2a, the control unit 6b controls the DC voltage to be supplied to the motor 6c. The control unit 6b controls, step by step or continuously, parameters such as the vibration frequency or the vibration wavelength, of the vibration caused by the later mentioned reciprocating motion.

The motor 6c is driven to rotate when the DC voltage is supplied. The type of the motor is an electric drive motor or a magnetic drive linear motor, for example. The converter 6d converts rotating motion of the motor 6c to reciprocating motion from the near side to the far side or from the far side to the near side in FIG. 2.

The control unit 6b controls the number of rotations of the motor 6c, and as a result, physical vibration of non-ultrasonic frequency can be generated on the converter 6d. The non-ultrasonic frequency is a frequency that enables the vibration to reach the lesion area in the body. Considering damping of the vibration caused by the rubber valve of the sheath 10b, the non-ultrasonic frequency should be more than 1 Hz and less than 20,000 Hz, for example. However, the non-ultrasonic frequency should preferably be 10 Hz to 2,000 Hz, more preferably be 15 Hz to 900 Hz. By specifying the frequency as described above, the guiding catheter 10a or the guide wire 10d can be pushed toward the lesion area with a smaller operating force.

Note that the control unit 6b can also be operated based on control signals output from a computer located outside the vibration imparting device 1. The computer records software programs for controlling the vibration imparting device 1. If the operator operates the computer, the computer accesses and executes the software programs to output the control signals.

In addition, variations of the physical vibration generated by the actuator 6 can be arbitrarily specified according to a position to be vibrated in the catheter system 10. The variations (modes) of the physical vibration to be specified are, for example, a mode for vibrating the guiding catheter 10a, a mode for vibrating the catheter to be inserted, or a mode for vibrating the guide wire 10d.

The vibration transmitting portion 3 is located on the base 2. On the vibration transmitting portion 3, the vibrating portion 4 is provided. The vibration transmitting portion 3 transfers the vibration generated by the actuator 6 to the vibrating portion 4.

The vibrating portion 4 has a first concave portion 4a and a second concave portion 4b that is sequentially provided with the first concave portion 4a. Surface area of the second concave portion 4b becomes smaller from the top to the bottom in the FIG. 2. The attachment mechanism 5, whose outer shape is formed to correspond with the shape of the second concave portion 4b, is placed in the second concave portion 4b. The attachment mechanism 5 is an example of the supporting portion that supports the insertion device to be inserted into the body. The attachment mechanism 5 is attached to the second concave portion 4b and is detachable from the second concave portion 4b. In FIG. 2, the attachment mechanism 5 contacts with a lateral portion 4b1 of the second concave portion 4b, and a space is provided between a bottom portion 4b2 of the second concave portion 4b and a bottom portion 5b of the attachment mechanism 5. Therefore, the attachment mechanism 5 is fixed by frictional force against the lateral portion 4b1 of the second concave portion 4b to restrict movement of the attachment mechanism 5.

The attachment mechanism 5 is made of, for example, petroleum based products such as a synthetic resin or a synthetic rubber, solid high molecular compounds, metals, or ceramics such as a ceramic compound.

The attachment mechanism 5 shown in FIG. 1 supports the guiding catheter 10a. The attachment mechanism 5 has a function to fix the guiding catheter 10a in place. For example, a concave portion 5a, whose outer shape is formed to correspond with the guiding catheter 10a, is provided on the attachment mechanism 5. An inner diameter of the concave portion 5a is a little larger than an outer diameter of the body of the guiding catheter 10a or an outer diameter of a branched portion of the branch connector. Therefore, after the guiding catheter 10a is inserted into the attachment mechanism 5, the guiding catheter 10a is fixed to the attachment mechanism 5 by frictional force. When a force exceeding the frictional force is applied, the guiding catheter 10a moves with contacting the concave portion 5a of the attachment mechanism 5, and as a result, the guiding catheter 10a is detachable.

Figure 3:
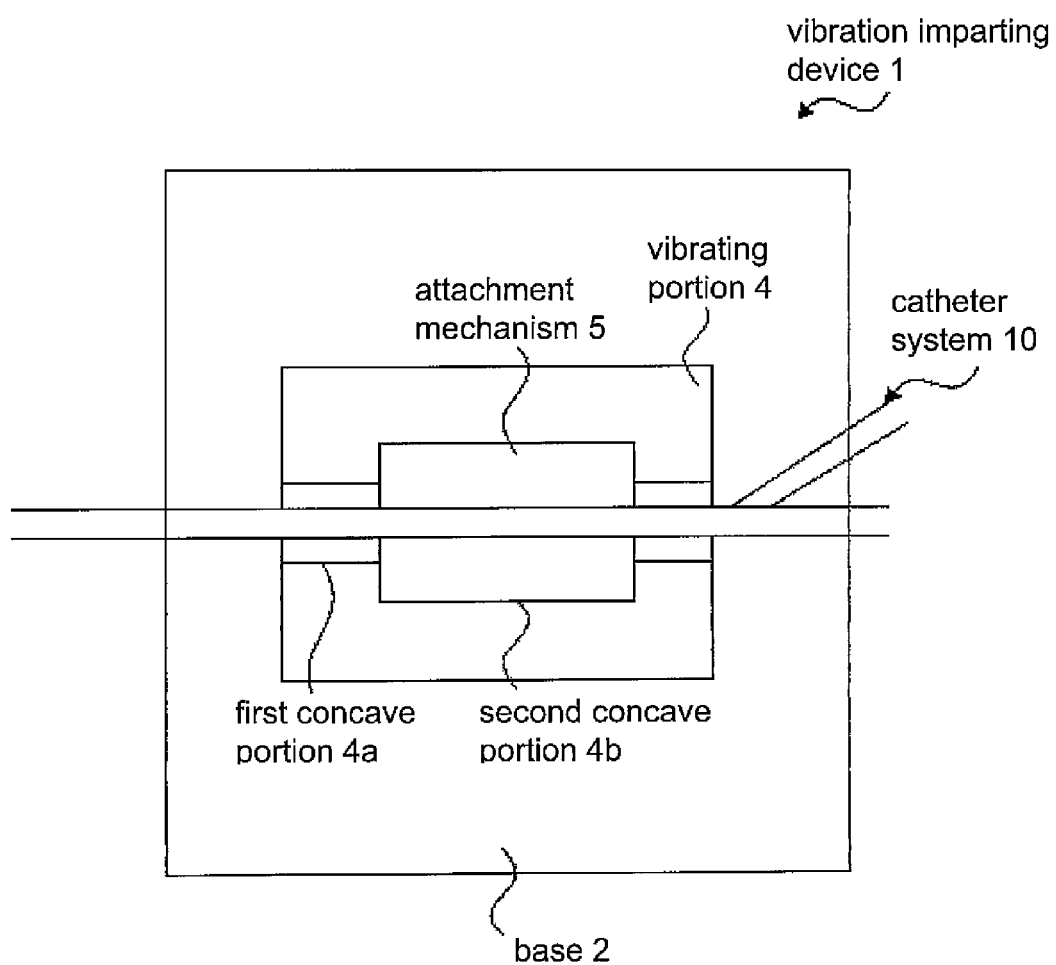
FIG. 3 shows a top view of the vibration imparting device.

Although only one attachment mechanism 5 is shown in FIG. 1, but in practice, plural attachment mechanisms are provided according to the shape and the outer diameter of the guiding catheters, and an appropriate attachment mechanism is selected according to the guiding catheter to be inserted. FIG. 3 shows a top view of the vibration imparting device.

A length of the vibrating portion 4 in horizontal direction shown in FIG. 3 is specified to have enough strength for supporting the attachment mechanism 5 even when the attachment mechanism 5 moves in horizontal direction.

In the present embodiment, the guiding catheter 10a is fixed to the attachment mechanism 5 by frictional force. However, the method for fixing the guiding catheter 10a to the attachment mechanism 5 is not limited to the frictional force. For example, a biasing force of a spring or a screw is available. If the guiding catheter 10a is fixed to the attachment mechanism 5 using the spring, an amount of movement of the guiding catheter 10a when the actuator 6 is driven can be adjusted by adjusting the biasing force of the spring.

The guiding catheter 10a does not have to be fixed on the attachment mechanism 5. The guiding catheter 10a can be mounted on the attachment mechanism 5 keeping a certain flexibility.

Figure 4:
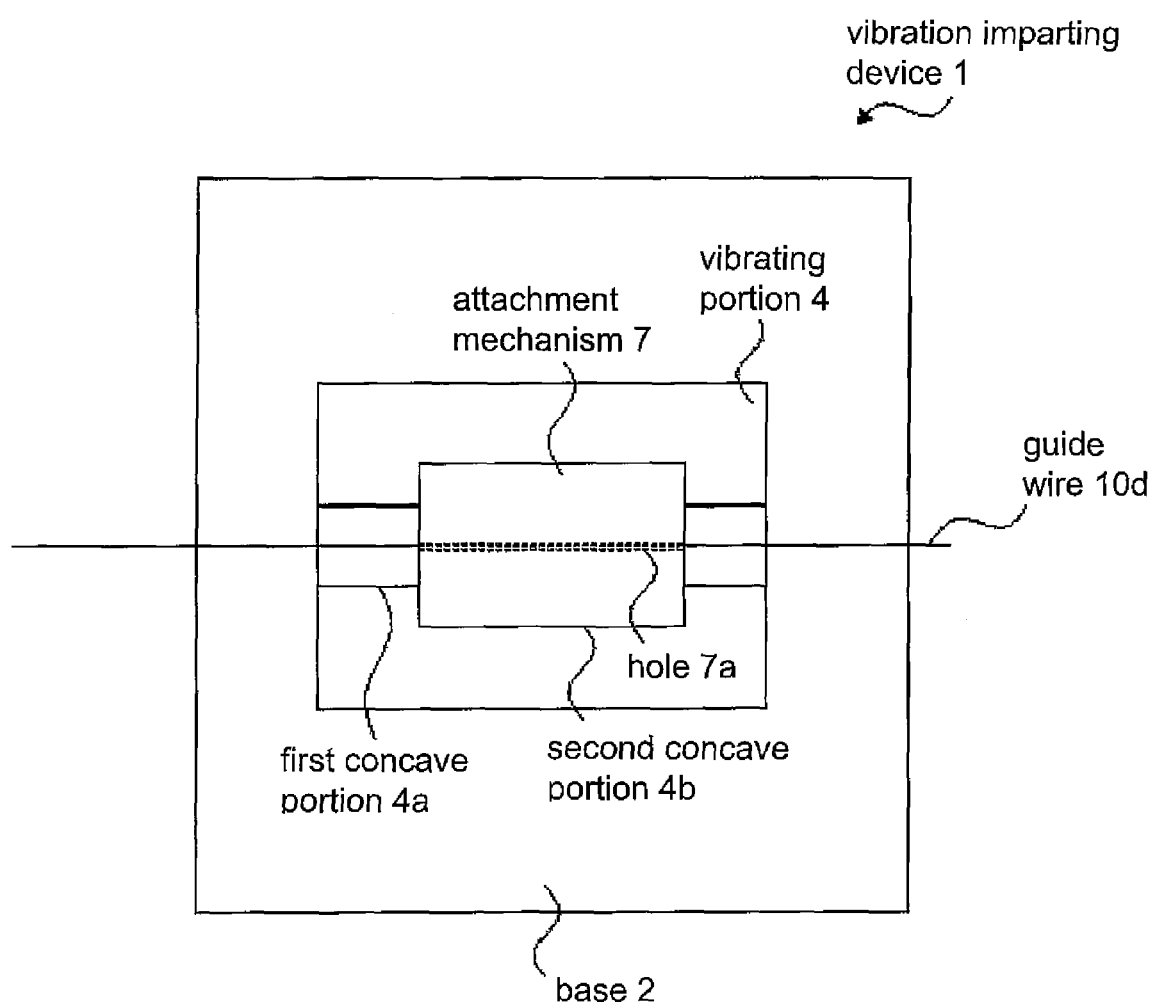
FIG. 4 shows a variation example of an attachment mechanism.

In the present embodiment, the attachment mechanism 5 supports the guiding catheter 10a. However, in the catheter system 10, a portion to be supported is not limited to the guiding catheter 10a. A hand operation portion for the catheter system, such as a catheter inserted into the guiding catheter 10a, can be supported, instead of the guiding catheter 10a. In addition, other attachment mechanisms can be prepared for attaching the guide wire 10d, a balloon catheter for expansion, a stent-balloon catheter for placement, a catheter for special operation, or other devices so as to impart vibration to an exposed portion of the devices in the same manner as for the guiding catheter 10a. The devises can be fixed or semi-fixed on the attachment mechanism or can be mounted on the attachment mechanism keeping a certain flexibility. FIG. 4 shows a variation example of the attachment mechanism.

An attachment mechanism 7 shown in FIG. 4 is used for imparting vibration to the guide wire 10d, instead of the guiding catheter 10a. The attachment mechanism 7 is made of rubber and formed to correspond with a shape of the second concave portion 4b. A hole 7a is formed at the center of the attachment mechanism 7 so as to insert the guide wire 10d.

The guide wire 10d is inserted into the hole 7a. An example of use of the vibration imparting device 1 will be explained below.

First, an operator performs generally known hand operations to place or delivery a catheter to a lesion area in the body of a patient. If the catheter can be placed to the lesion area to be treated, the operator continues the operation without using the vibration imparting device 1. On the other hand, if the catheter cannot be placed easily to the lesion area to be treated, the vibration imparting device 1 is used. As for blood vessels, difficulty to place the catheter is caused by morphological factors such as a stenosis or physical factors such as a calcification, for example.

The operator sets up the guiding catheter 10a of the catheter system 10, which is already prepared to be used, on the concave portion 5a of the attachment mechanism 5. When using the catheter system 10, it is necessary to maintain cleanliness of a sterilized operating field. Therefore, components of the vibration imparting device 1 should be previously sterilized. As for components of the vibration imparting device 1 that are difficult to be sterilized, sterile condition is maintained by using an existing method, such as covering the components with a sterilized plastic bag. While maintaining this state, the guiding catheter 10a is set up on the concave portion 5a of the attachment mechanism 5.

The location of the vibration imparting device 1 can be selected arbitrarily. By locating the vibration imparting device 1 not to prevent the operator from operating the catheter using his/her technique, the operator can perform hand operations creatively and originally. For example, as shown in FIG. 1, the vibration imparting device 1 is located near the sheath 10b and the operator grasps the guide wire 10d from the right side of FIG. 1.

The operator turns on a switch provided on the operating portion 2a of the vibration imparting device 1, and then selects one of the preliminarily specified operation modes. Then, the operator adjusts the parameters of actual vibration such as a vibration frequency or a vibration wavelength. Next, the operator turns on a switch to start vibrating. The actuator 6 is driven, and vibration of non-ultrasonic frequency in horizontal direction in FIG. 3, which is caused by reciprocating motion along an insertion/removal direction of the guiding catheter 10a, is imparted to the guiding catheter 10a via the vibrating portion 4 and the attachment mechanism 5. While maintaining this state, the operator grasps a catheter to be inserted into the guiding catheter 10a, such as a catheter wire or a balloon catheter, and then inserts the catheter in a forward direction. By doing so, the catheter is prevented from being caught in the lesion area, and the catheter can be more certainly inserted through the lesion area. Consequently, the operator can insert the catheter in the forward direction more easily.

The present invention uses a widely recognized principle of natural science that frictional resistance is changed from "static friction" to relatively simple "dynamic friction" by imparting physical vibration. In addition, the present invention also uses a principle of natural science that the imparted vibration can be transferred to the catheter or the guide wire to be inserted via whole the catheter system 10. Because of the principles above, frictional resistance including physical scratching resistance can be reduced between the catheter to be inserted into the body and the guiding catheter 10a, between the catheter to be inserted into the body and the lesion area, or between the guide wire 10d or similar catheters to be inserted and the lesion area. As a result, the catheter wire or the balloon catheter can reach and pass through the lesion area to some extent, and then normal catheterization, which is conventionally and widely employed, can be restarted. Next, a practical example of the vibration imparting device 1 will be explained. A magnetic drive linear motor having a nominal frequency of 14,000 strokes per minute was mounted on the vibration imparting device of the practical example.

A test model of a coronary artery vessel was prepared. Then, an operator operated a catheter system and tried to place a catheter on a lesion area of the test model to be treated without using the vibration imparting device. An operating force required for pushing the catheter toward the lesion area was measured by using a digital force gauge (DPX-5T, manufactured by IMADA CO., LTD.).

Next, the operator operated the catheter system and tried to place the catheter on the lesion area of the test model to be treated using the vibration imparting device. An operating force required for pushing the catheter toward the lesion area was measured by using the digital force gauge As a result, although the operating force required was 1.27 N when the vibration imparting device was not used, the operating force was reduced to 0.57 N when the vibration imparting device was used. The operating force is reduced by 56% compared to the operating force required when the vibration imparting device was not used. After that, the same experiments were repeated and similar results were obtained. Therefore, an actual effect of the vibration imparting device was proved.

As described above, by using the vibration imparting device 1, physical vibration generated at the outside body can be transferred via the guiding catheter 10a to vibrate the guide wire 10d. As a result, frictional resistance including physical scratching resistance can be reduced between the guide wire 10d inserted into the body and the lesion area.

In addition, the vibration imparting device 1 is an assist device that can be added later in case the operation of the catheter is difficult. Therefore, the operator can decide arbitrarily whether or not to use the vibration imparting device 1 according to a situation.

Furthermore, frequency to change the catheter can be reduced because failures when the catheter path through the lesion area are reduced. If the catheter is replaced, an additional cost of 100,000 yen to 400,000 yen per one catheter may be required. Normally, catheter wires and catheters failed to pass thorough the lesion area cannot be reused, and they are generally disposed of. Therefore, if the frequency to change the catheter is reduced, medical expenses can be reduced.

Furthermore, because the existing catheter can be used without change, various technological innovations and problem resolutions in the past, which were historically made to develop catheterization, can be used without change.

To insert the catheter into the lesion area correctly and to place the catheter on a proper position is one of the most important points in order to finish catheter operation successfully. In this regard, the present invention can provide higher operability and safety by reducing skill gap between skilled operators and normal operators.

In general, an operation portion of the catheter is located at a distance from a tip of the catheter because the operating portion cannot be placed near the lesion area to be treated in the body. In addition, the sheath is interposed between the operating portion of the catheter and the tip of the catheter. When the operator produces the vibration by hand, frequency of the vibration is about 1 to 15 Hz. Therefore, even when the operator produces the vibration by hand, the vibration is decreased by the sheath, and therefore the vibration is not transferred to the tip of the catheter or transferred after decreased significantly. By using the vibration imparting device 1, the vibration is transferred to the tip of the catheter much more efficiently compared to the hand operation of the catheter. Furthermore, the vibration can be easily adjusted considering individual difference of living bodies such as an amount of subcutaneous fat, a shape of vessel, or a property of vessel, and considering natural frequency of the catheter depending on material or structure of existing catheter.

Because the operator does not have to produce the vibration if the vibration imparting device 1 is used, the operator can concentrate on hand operations which are fundamentally important. Therefore, the operator can treat some cases even when they were conventionally difficult to perform a catheterization.

The vibration imparting device of the present invention is explained based on the embodiment shown in the figures, but the present invention is not limited to the above-mentioned embodiments. Of course, the components of the present invention can be replaced by other equivalent components. Also, other components and processes can be arbitrarily added to the present invention. Also, the present invention can be achieved by combining two or more embodiments or features described above.

The intended purpose of the vibration imparting device of the present invention is not limited to the catheter system. The vibration imparting device can be also applied to, for example, an insertion part of an endoscope, a medical tubing such as a stomach tube, a medical cable such as an electrode of a pacemaker, a forceps, a medical scissors, or a medical knife.

What is claimed is:

1. A vibration imparting device comprising:
    a supporting portion that supports an insertion device to be inserted into a body; and
    a vibrating portion that is located outside the body and imparts vibration of non-ultrasonic frequency to the insertion device via the supporting portion,
    wherein the vibration portion includes a first concave portion opening upwardly so that the supporting portion is attached to the first concave portion from above.

2. The vibration imparting device according to claim 1, wherein the vibrating portion imparts vibration caused by reciprocating motion along an insertion direction and a removal direction of the insertion device.

3. The vibration imparting device according to claim 1, wherein the supporting portion is attachable/detachable to/from the vibrating portion.

4. The vibration imparting device according to claim 1, wherein the supporting portion has a second concave portion formed to correspond with a shape of the insertion device; and the insertion device is movable contacting the second concave portion while the vibrating portion imparts the vibration to the supporting portion.

5. The vibration imparting device according to claim 1, wherein the supporting portion has a hole formed to correspond with a shape of the insertion device, and the insertion device is movable contacting the hole while the vibrating portion imparts the vibration to the supporting portion.

6. The vibration imparting device according to claim 1, wherein the vibration portion includes a third concave portion opening upwardly so that the insertion device is accommodated in the third concave portion.

7. The vibration imparting device according to claim 6, wherein the first concave portion is communicated with the third concave portion.

8. The vibration imparting device according to claim 6, wherein the first concave portion has a width corresponding to that of the supporting portion in a plan view, and
    the width of the first concave is greater than that of the third concave portion in the plan view.

9. The vibration imparting device according to claim 6, wherein the first concave portion is formed between a front portion and a rear portion of the third concave portion.

10. The vibration imparting device according to claim 6, wherein the first concave portion has a depth so that a bottom surface of the supporting portion is away from a bottom surface of the first concave portion when the supporting portion is attached to the first concave portion from above.

* * * * *